United States Patent
Ichinose (10) Patent No.: US 12,387,825 B2
(45) Date of Patent: Aug. 12, 2025

(54) INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventor: Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 361 days.

(21) Appl. No.: 17/888,423

(22) Filed: Aug. 15, 2022

(65) Prior Publication Data

US 2022/0392595 A1 Dec. 8, 2022

Related U.S. Application Data

(63) Continuation of application No. PCT/JP2021/006196, filed on Feb. 18, 2021.

(30) Foreign Application Priority Data

Feb. 18, 2020 (JP) .................. 2020-025672

(51) Int. Cl.
  *G16H 10/60* (2018.01)
  *G06T 7/00* (2017.01)
  *G06V 10/776* (2022.01)
  *G06V 20/70* (2022.01)
  (Continued)

(52) U.S. Cl.
  CPC ........... *G16H 15/00* (2018.01); *G06T 7/0012* (2013.01); *G06V 10/776* (2022.01); *G06V 20/70* (2022.01); *G06T 2207/20081* (2013.01); *G06T 2207/30096* (2013.01); *G06V 2201/032* (2022.01)

(58) Field of Classification Search
  USPC ................ 128/915–916, 920, 922–925; 382/103–104, 128–133, 151–159
  See application file for complete search history.

(56) References Cited

U.S. PATENT DOCUMENTS

| | | | |
|---|---|---|---|
| 10,970,365 B2 | 4/2021 | Sorenson et al. | |
| 2017/0124424 A1* | 5/2017 | Takahashi | G06V 20/10 |
| 2018/0101645 A1 | 4/2018 | Sorenson et al. | |

(Continued)

FOREIGN PATENT DOCUMENTS

| | | |
|---|---|---|
| JP | 2017167738 | 9/2017 |
| JP | 2018110040 | 7/2018 |

(Continued)

OTHER PUBLICATIONS

Shiraishi Yasushi; Endoscope System, Processor Device for Endoscope System, Operation Method for Endoscope System, and Operation Method for Processor Device; 2015 (Year: 2015).*

(Continued)

*Primary Examiner* — Marcellus J Augustin
(74) *Attorney, Agent, or Firm* — JCIPRNET (57) ABSTRACT

An information processing apparatus comprising at least one processor, wherein the at least one processor is configured to: determine a property of a predetermined property item from at least one image; generate a plurality of character strings related to the at least one image from the at least one image; and derive a recommended score indicating a degree of recommendation for describing the character string in a document for each of the plurality of character strings based on a result of the determination.

10 Claims, 9 Drawing Sheets

(51) Int. Cl.
*G16H 15/00* (2018.01)
*G16H 30/40* (2018.01)

(56) References Cited

U.S. PATENT DOCUMENTS

| | | | | |
|---|---|---|---|---|
| 2018/0166167 | A1* | 6/2018 | Kanada | G06T 7/0012 |
| 2019/0279751 | A1* | 9/2019 | Nakamura | G16H 30/40 |
| 2019/0374088 | A1* | 12/2019 | Watanabe | A61B 1/0638 |
| 2020/0111545 | A1* | 4/2020 | Syeda-Mahmood | G16H 15/00 |
| 2020/0265265 | A1* | 8/2020 | Yoshizuka | G06F 18/28 |
| 2020/0411150 | A1 | 12/2020 | Saalbach et al. | |

FOREIGN PATENT DOCUMENTS

| | | |
|---|---|---|
| JP | 2019153250 | 9/2019 |
| JP | 2019536132 | 12/2019 |
| WO | 2018012090 | 1/2018 |
| WO | 2018159363 | 9/2018 |
| WO | 2019134872 | 7/2019 |

OTHER PUBLICATIONS

Matsumasa Hironori; Medical Report Evaluation Device, Medical Report Evaluation Method, Medical Report Evaluation Program and Medical Network System; 2012 (Year: 2012).*

"International Search Report (Form PCT/ISA/210) of PCT/JP2021/006196," mailed on May 11, 2021, with English translation thereof, pp. 1-6.

"Written Opinion of the International Searching Authority (Form PCT/ISA/237)" of PCT/JP2021/006196, mailed on May 11, 2021, with English translation thereof, pp. 1-10.

Office Action of Japan Counterpart Application, with English translation thereof, issued on Sep. 19, 2023, pp. 1-8.

* cited by examiner

| PROPERTY ITEM | DETERMINATION |
|---|---|
| MARGIN/LOBULAR | + |
| MARGIN/SPICULA | − |
| ABSORPTION VALUE/SOLID | + |
| ABSORPTION VALUE/FROSTED GLASS | − |
| BOUNDARY UNCLEAR | − |
| CALCIFICATION | − |
| PLEURAL INVAGINATION | − |
| ⋮ | ⋮ |

FIG. 6

[CANDIDATE A]
SOLID NODULE WITH MAJOR AXIS
OF 21 mm IS FOUND IN RIGHT UPPER LOBE S3.
IT IS LOBULAR. NO CALCIFICATION IS FOUND.

[CANDIDATE B]
SOLID NODULE WITH MAJOR AXIS
OF 21 mm IS FOUND IN RIGHT UPPER LOBE S3.
IT IS ACCOMPANIED BY SPICULA.
NO CALCIFICATION IS FOUND.

[CANDIDATE C]
SOLID NODULE WITH MAJOR AXIS
OF 21 mm IS FOUND IN RIGHT UPPER LOBE S3.
NO PLEURAL INVAGINATION IS FOUND.

[CANDIDATE D]
SOLID NODULE WITH MAJOR AXIS
OF 21 mm IS FOUND IN RIGHT UPPER LOBE S3.
IT IS LOBULAR AND. NO CALCIFICATION IS FOUND.

FIG. 7

| COMMENTS ON FINDINGS | FIRST SCORE | SECOND SCORE | THIRD SCORE | RECOMMENDED SCORE |
|---|---|---|---|---|
| CANDIDATE A | 1.0 | 1.0 | 1.0 | 1.00 |
| CANDIDATE B | 0.4 | 1.0 | 1.0 | 0.76 |
| CANDIDATE C | 1.0 | 0.6 | 1.0 | 0.92 |
| CANDIDATE D | 1.0 | 1.0 | 0.2 | 0.68 |
| | (× 0.4) | (× 0.2) | (× 0.4) | |

```
INFORMATION PROCESSING
        │
   ACQUIRE IMAGE                              ~S10
        │
   DETERMINE PROPERTY OF
   PROPERTY ITEM FROM IMAGE                   ~S12
        │
   GENERATE COMMENTS ON FINDINGS FROM IMAGE   ~S14
        │
   DERIVE RECOMMENDED SCORE                   ~S16
        │
   DISPLAY COMMENTS ON FINDINGS ON DISPLAY    ~S18
        │
       END
```

FIG. 10

| PROPERTY ITEM | DETERMINATION | FOURTH SCORE |
|---|---|---|
| MARGIN/LOBULAR | + | 0.65 |
| MARGIN/SPICULA | - | 0.42 |
| ABSORPTION VALUE/SOLID | + | 0.98 |
| ABSORPTION VALUE/FROSTED GLASS | - | 0.20 |
| BOUNDARY UNCLEAR | - | 0.23 |
| CALCIFICATION | - | 0.08 |
| PLEURAL INVAGINATION | - | 0.11 |
| ⋮ | ⋮ | ⋮ |

FIG. 11

| COMMENTS ON FINDINGS | REPRESENTATIVE VALUE OF FOURTH SCORE | RECOMMENDED SCORE |
|---|---|---|
| CANDIDATE A | {0.98 + 0.65 + (1 − 0.08)}/3 = 0.85 | 0.85 |
| CANDIDATE B | {0.98 + 0.42 + (1 − 0.08)}/3 = 0.77 | 0.77 |
| CANDIDATE C | {0.98 + (1 − 0.11)}/2 = 0.94 | 0.94 |
| CANDIDATE D | {0.98 + 0.65 + (1 − 0.08)}/3 = 0.85 | 0.85 |

FIG. 12

| RULE LIST |
|---|
| ESSENTIAL/SHAPE OF MARGIN |
| ESSENTIAL/CALCIFICATION |
| ALL POSITIVE PROPERTY ITEMS |

FIG. 13

| COMMENTS ON FINDINGS | FIFTH SCORE | RECOMMENDED SCORE |
|---|---|---|
| CANDIDATE A | 1.0 | 1.00 |
| CANDIDATE B | 0.6 | 0.60 |
| CANDIDATE C | 0.1 | 0.10 |
| CANDIDATE D | 1.0 | 1.00 |

FIG. 14

| | RULE LIST |
|---|---|
| ✔ | ESSENTIAL/SHAPE OF MARGIN |
| ✔ | ESSENTIAL/CALCIFICATION |
| | ESSENTIAL/PLEURAL INVAGINATION |
| ✔ | ALL POSITIVE PROPERTY ITEMS |
| | POSITIVE PROPERTY ITEM WITH FOURTH SCORE OF 0.8 OR HIGHER |
| | ⋮ |

FIG. 15

| RULE LIST | SIXTH SCORE |
|---|---|
| ESSENTIAL/SHAPE OF MARGIN | 0.95 |
| ESSENTIAL/CALCIFICATION | 0.88 |
| ESSENTIAL/PLEURAL INVAGINATION | 0.21 |
| ALL POSITIVE PROPERTY ITEMS | 0.93 |
| POSITIVE PROPERTY ITEM WITH FOURTH SCORE OF 0.8 OR HIGHER | 0.33 |
| ⋮ | ⋮ |

FIG. 16

| COMMENTS ON FINDINGS | FIFTH SCORE | RECOMMENDED SCORE |
|---|---|---|
| CANDIDATE A | {0.95 + 0.88 + 0.93}/3 = 0.92 | 0.92 |
| CANDIDATE B | {0.95 + 0.88 + 0.33}/3 = 0.72 | 0.72 |
| CANDIDATE C | {0.21 + 0.33}/2 = 0.27 | 0.27 |
| CANDIDATE D | {0.95 + 0.88 + 0.93}/3 = 0.92 | 0.92 |

FIG. 17

| COMMENTS ON FINDINGS | FIRST SCORE | SECOND SCORE | THIRD SCORE | REPRESENTATIVE VALUE OF FOURTH SCORE | FIFTH SCORE | RECOMMENDED SCORE |
|---|---|---|---|---|---|---|
| CANDIDATE A | 1.0 | 1.0 | 1.0 | 0.85 | 1.0 | 0.97 |
| CANDIDATE B | 0.4 | 1.0 | 1.0 | 0.77 | 0.6 | 0.75 |
| CANDIDATE C | 1.0 | 0.6 | 1.0 | 0.94 | 0.1 | 0.77 |
| CANDIDATE D | 1.0 | 1.0 | 0.2 | 0.85 | 1.0 | 0.73 |
| | (× 0.2) | (× 0.1) | (× 0.3) | (× 0.2) | (× 0.2) | |

INFORMATION PROCESSING APPARATUS, INFORMATION PROCESSING METHOD, AND INFORMATION PROCESSING PROGRAM

CROSS REFERENCE TO RELATED APPLICATIONS

The present application is a Continuation of PCT International Application No. PCT/JP2021/006196, filed on Feb. 18, 2021, which claims priority to Japanese Patent Application No. 2020-025672, filed on Feb. 18, 2020. Each application above is hereby expressly incorporated by reference, in its entirety, into the present application.

BACKGROUND

Technical Field

The present disclosure relates to an information processing apparatus, an information processing method, and an information processing program for supporting creation of documents such as interpretation reports.

Related Art

In recent years, advances in medical devices, such as computed tomography (CT) apparatuses and magnetic resonance imaging (MM) apparatuses, have enabled image diagnosis using high-resolution medical images with higher quality. In particular, since a region of a lesion can be accurately specified by image diagnosis using CT images, MRI images, and the like, appropriate treatment is being performed based on the specified result.

In addition, image diagnosis is made by analyzing a medical image via computer-aided diagnosis (CAD) using a discriminator in which learning is performed by deep learning or the like, and discriminating properties such as the shape, density, position, and size of a structure of interest such as a lesion included in the medical image. The analysis result obtained in this way is saved in a database in association with examination information, such as a patient name, gender, age, and an imaging apparatus which has acquired a medical image. The medical image and the analysis result are transmitted to a terminal of a radiologist who interprets the medical images. The radiologist interprets the medical image by referring to the distributed medical image and analysis result and creates an interpretation report, in his or her own interpretation terminal.

Meanwhile, with the improvement of the performance of the CT apparatus and the MRI apparatus described above, the number of medical images to be interpreted is increasing. Therefore, in order to reduce the burden of the interpretation work of a radiologist, various methods have been proposed to support the creation of medical documents such as interpretation reports. For example, a method for generating a sentence to be included in an interpretation report based on keywords input by a radiologist and on information indicating a property of a structure of interest such as a lesion (hereinafter referred to as property information) included in an analysis result of a medical image is disclosed (see JP2019-153250A). In the technique described in JP2019-153250A, a sentence to be described in the interpretation report is created by using a learning model in which machine learning is performed, such as a recurrent neural network trained to generate a sentence from characters representing the input property information.

However, the content of the sentence generated by the learning model described in JP2019-153250A does not always match the properties of the structure of interest such as a lesion included in the medical image. For example, it is assumed that the learning model learns a lot of learning data in which "solidity" and "spicula" are included in the same sentence as learning data related to nodular shadows. In this case, if a "solid" nodular shadow is found in the medical image for which the sentence is generated, a sentence including "solidity" and "spicula" may be generated in some cases even though "spicula" is not found in the nodular shadow.

SUMMARY

The present disclosure provides an information processing apparatus, an information processing method, and an information processing program capable of supporting creation of documents such as interpretation reports.

According to a first aspect of the present disclosure, there is provided an information processing apparatus comprising at least one processor, in which the processor is configured to determine a property of a predetermined property item from at least one image, generate a plurality of character strings related to the image from the image, and derive a recommended score indicating a degree of recommendation for describing the character string in a document for each of the plurality of character strings based on a result of the determination.

According to a second aspect of the present disclosure, in the above aspect, the processor may be configured to, for each of the plurality of character strings, derive a first score indicating a degree to which a content of the character string matches the result of the determination, a second score indicating a degree to which the number of characters included in the character string or the number of items corresponding to the property items included in the character string is appropriate, and a third score indicating a degree of fluency of the character string, and derive the recommended score based on the first to third scores.

According to a third aspect of the present disclosure, in the above aspect, the processor may be configured to derive a fourth score indicating a prominence of the property from the image, and derive the recommended score based on the fourth score corresponding to the item corresponding to the property item included in the character string.

According to a fourth aspect of the present disclosure, in the above aspect, the processor may be configured to, for each of the plurality of character strings, derive a fifth score indicating a degree to which a content of the character string conforms to a predetermined rule, and derive the recommended score based on the fifth score.

According to a fifth aspect of the present disclosure, in the above fourth aspect, the rule may be a rule predetermined by a user.

According to a sixth aspect of the present disclosure, in the above fourth and fifth aspects, the processor may be configured to, for each of a plurality of predetermined rules, derive a sixth score indicating a degree to which a content of a character string for analysis conforms to the rule, and for each of the plurality of character strings, derive the fifth score by using the sixth score of the rule to which the content of the character string conforms.

According to a seventh aspect of the present disclosure, in the above aspect, the processor may be configured to perform control such that at least one character string and the recommended score corresponding to the character string are displayed on a display.

According to an eighth aspect of the present disclosure, in the above aspect, the processor may be configured to perform control such that the plurality of character strings are displayed on the display by arranging the plurality of character strings in an order of the recommended scores.

According to a ninth aspect of the present disclosure, in the above aspect, the processor may be configured to perform control such that the character string having the recommended score equal to or higher than a predetermined threshold value among the plurality of character strings is displayed on the display.

According to a tenth aspect of the present disclosure, in the above aspect, the processor may be configured to perform control such that the character string having a highest recommended score among the plurality of character strings is emphasized and displayed on the display.

According to an eleventh aspect of the present disclosure, there is provided an information processing method comprising: determining a property of a predetermined property item from at least one image; generating a plurality of character strings related to the image from the image; and deriving a recommended score indicating a degree of recommendation for describing the character string in a document for each of the plurality of character strings based on a result of the determination.

According to a twelfth aspect of the present disclosure, there is provided an information processing program for causing a computer to execute a process comprising: determining a property of a predetermined property item from at least one image; generating a plurality of character strings related to the image from the image; and deriving a recommended score indicating a degree of recommendation for describing the character string in a document for each of the plurality of character strings based on a result of the determination.

According to the above aspects, the information processing apparatus, information processing method, and information processing program of the present disclosure can support the creation of documents such as interpretation reports.

DETAILED DESCRIPTION

Hereinafter, each exemplary embodiment of the present disclosure will be described with reference to the drawings.

First Exemplary Embodiment

First, a configuration of a medical information system 1 to which an information processing apparatus of the present disclosure is applied will be described.

Figure 1:
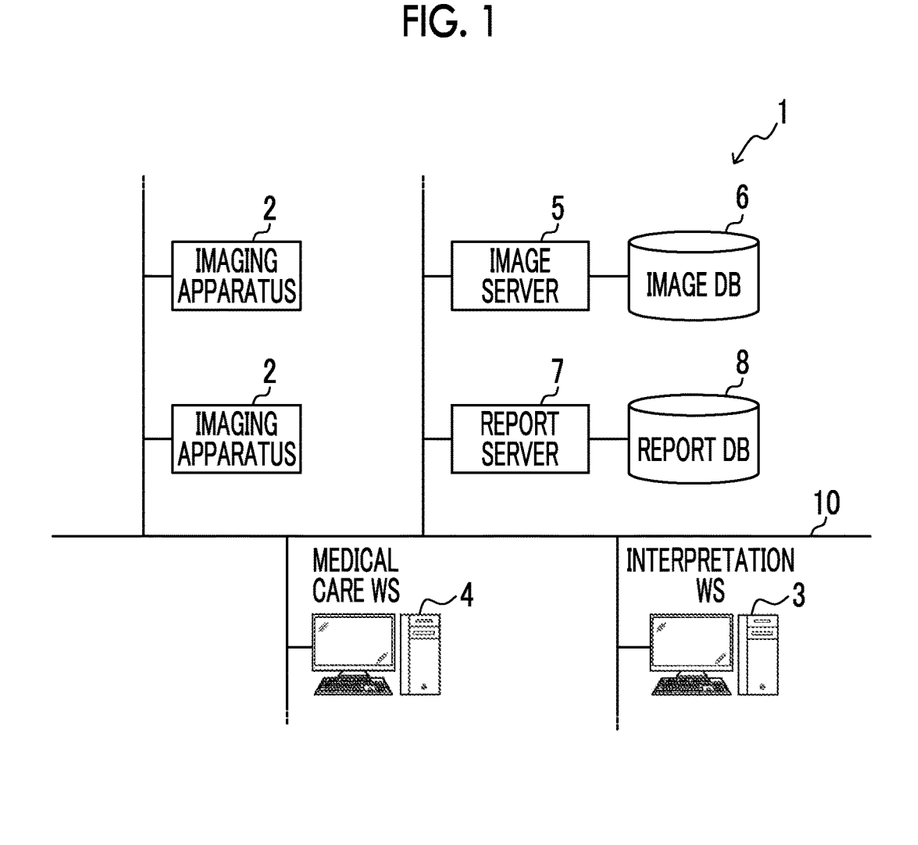
FIG. 1 is a diagram showing an example of a schematic configuration of a medical information system according to each exemplary embodiment.

FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, the medical information system 1 is configured to include a plurality of imaging apparatuses 2, a plurality of interpretation work stations (WS) 3 that are interpretation terminals, a medical care WS 4, an image server 5, an image database (DB) 6, a report server 7, and a report DB 8, which are connected via a wired or wireless network 10 so as to be able to communicate with each other.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 10 or in a network storage in a state in which it can be accessed from the outside, and is downloaded and installed on the computer in response to a request.

The imaging apparatus 2 is an apparatus (modality) that generates a medical image showing a diagnosis target part of the subject by imaging the diagnosis target part. Specifically, examples of the imaging apparatus include a simple X-ray imaging apparatus, a CT apparatus, an MRI apparatus, a positron emission tomography (PET) apparatus, and the like.

The medical image generated by the imaging apparatus 2 is transmitted to the image server 5 and is saved in the image DB 6.

The interpretation WS 3 is a computer used by, for example, a radiologist of a radiology department to interpret a medical image and to create an interpretation report, and encompasses an information processing apparatus 20 (which will be described in detail later) according to the present exemplary embodiment. In the interpretation WS 3, a viewing request for a medical image to the image server 5, various image processing for the medical image received from the image server 5, display of the medical image, and input reception of comments on findings regarding the medical image are performed. In the interpretation WS 3, an analysis process for medical images, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by, for example, a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including at least the comments on findings created by the radiologist using the interpretation WS 3 is registered. The interpretation report may include, for example, information such as a medical image to be interpreted, an image ID for identifying the medical image, a radiologist ID for identifying the radiologist who performed the interpretation, a lesion name, lesion position information, and a result of determining a property (which will be described in detail later).

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Next, the information processing apparatus 20 according to the present exemplary embodiment will be described.

Figure 2:
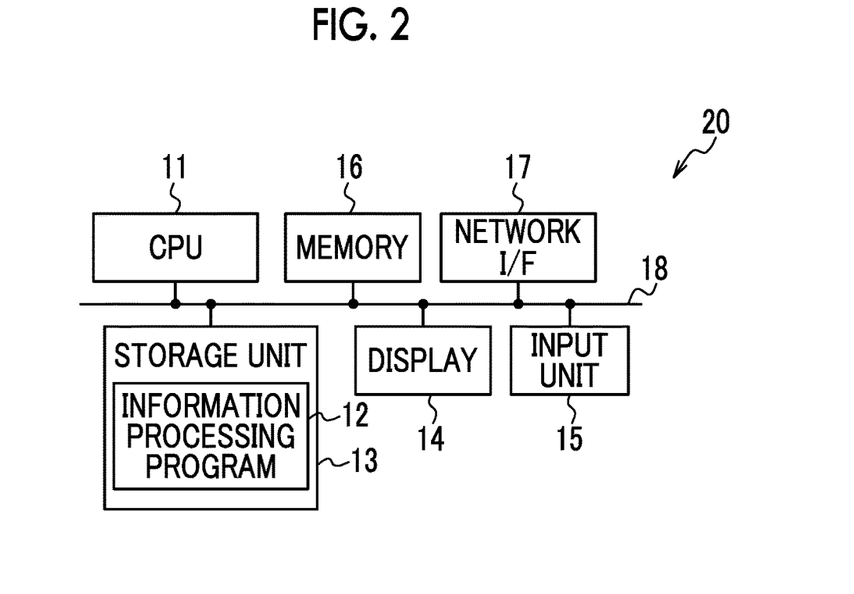
FIG. 2 is a block diagram showing an example of a hardware configuration of an information processing apparatus according to each exemplary embodiment.

First, with reference to FIG. 2, a hardware configuration of the information processing apparatus 20 according to the present exemplary embodiment will be described. As shown in FIG. 2, the information processing apparatus 20 includes a central processing unit (CPU) 11, a non-volatile storage unit 13, and a memory 16 as a temporary storage area. Further, the information processing apparatus 20 includes a display 14 such as a liquid crystal display and an organic electro luminescence (EL) display, an input unit 15 such as a keyboard and a mouse, and a network interface (I/F) 17 connected to the network 10. The CPU 11, the storage unit 13, the display 14, the input unit 15, the memory 16, and the network I/F 17 are connected to a bus 18. The CPU 11 is an example of a processor in the present disclosure.

The storage unit 13 is realized by a storage device such as a hard disk drive (HDD), a solid state drive (SSD), and a flash memory. An information processing program 12 is stored in the storage unit 13 as the storage medium. The CPU 11 reads out the information processing program 12 from the storage unit 13, loads the read-out program into the memory 16, and executes the loaded information processing program 12.

Figure 3:
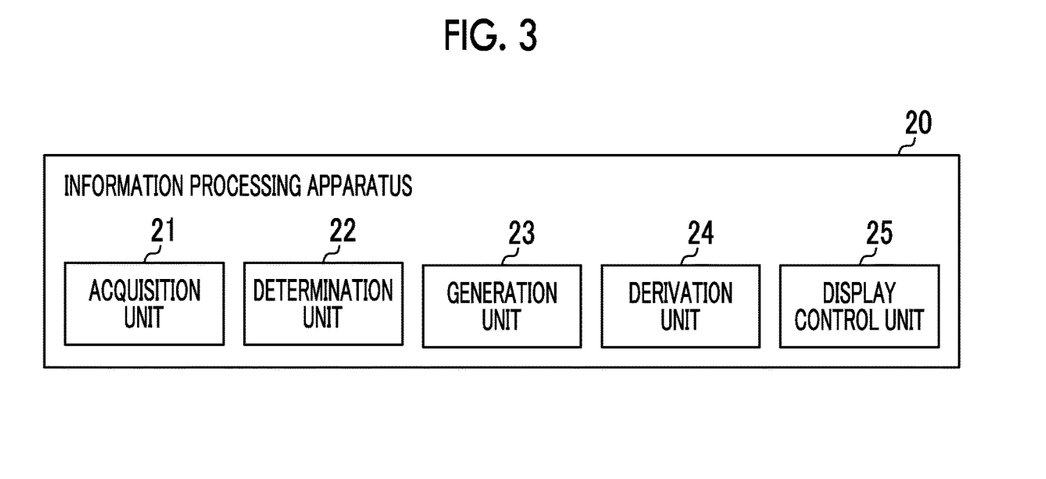
FIG. 3 is a block diagram showing an example of a functional configuration of the information processing apparatus according to each exemplary embodiment.

Next, with reference to FIGS. 3 to 8, a functional configuration of the information processing apparatus 20 according to the present exemplary embodiment will be described. As shown in FIG. 3, the information processing apparatus 20 includes an acquisition unit 21, a determination unit 22, a generation unit 23, a derivation unit 24, and a display control unit 25. The CPU 11 executing the information processing program 12 functions as the acquisition unit 21, the determination unit 22, the generation unit 23, the derivation unit 24, and the display control unit 25.

Figure 4:
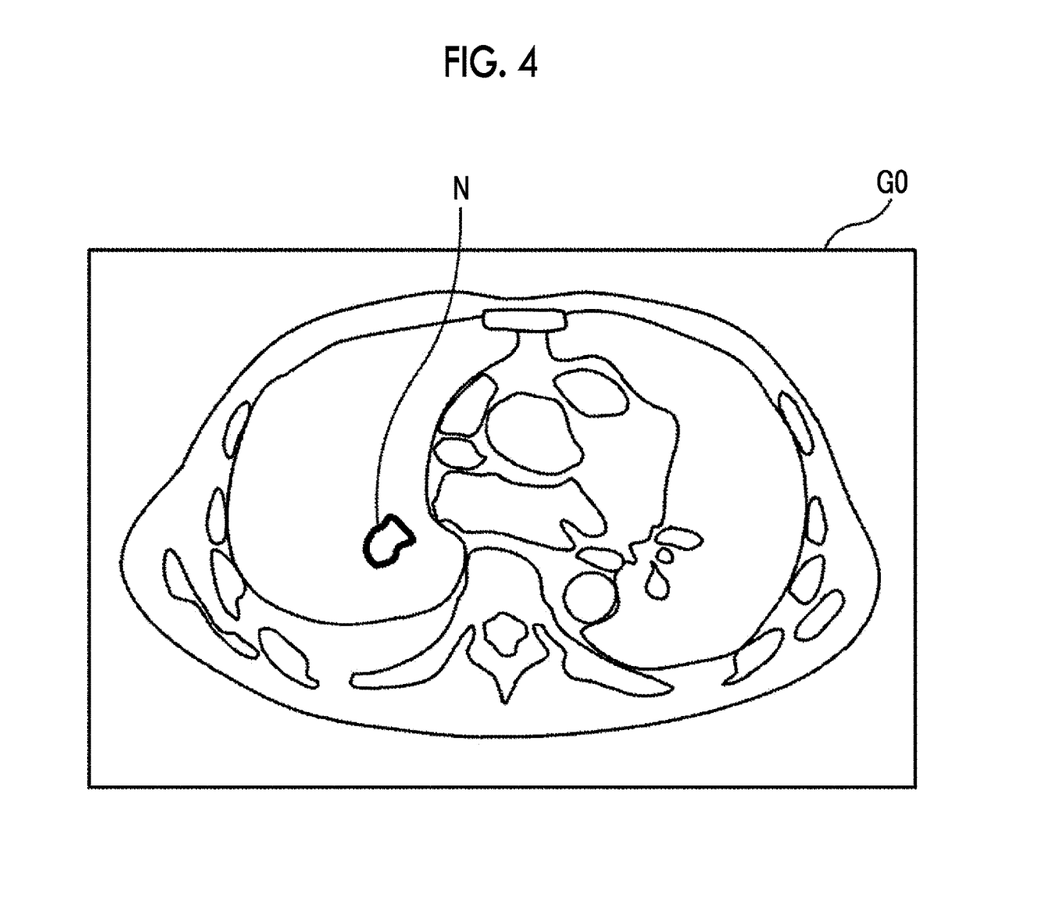
FIG. 4 is a diagram schematically showing a medical image.

The acquisition unit 21 acquires a medical image G0 as an example of the image from the image server 5 via the network I/F 17. FIG. 4 is a diagram schematically showing the medical image G0. In the present exemplary embodiment, as an example, a CT image of a lung is used as the medical image G0. The medical image G0 includes a nodular shadow N as an example of a structure of interest such as a lesion.

Figure 5:
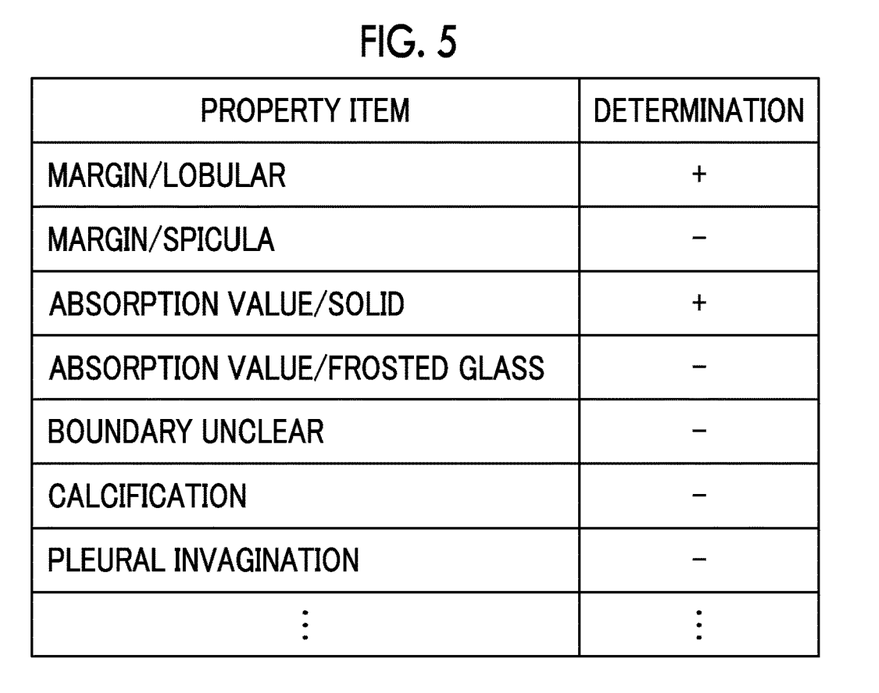
FIG. 5 is a diagram for describing a process of determining a property of a property item.

The determination unit 22 determines the properties of predetermined property items from at least one medical image G0. Specifically, the determination unit 22 analyzes the medical image G0 via CAD or the like, and specifies the position, type, and size of the lesion included in the medical image G0. Then, it is determined whether the property of the predetermined property item related to the specified lesion is positive or negative. That is, the property item is an item that is predetermined and stored in the storage unit 13 according to at least one of the position, type, or size of the lesion. FIG. 5 shows a predetermined property item related to the nodular shadow N and a property determination result of each property item performed by the determination unit 22. The property items related to the nodular shadow N include, for example, the shape of the margin (lobular or spicula), absorption value (solidity or frosted glass), clarity of the boundary, presence or absence of calcification, presence or absence of pleural invagination, and the like. In FIG. 5, "+" means that the property is positive, and "−" means that the property is negative.

Figure 6:
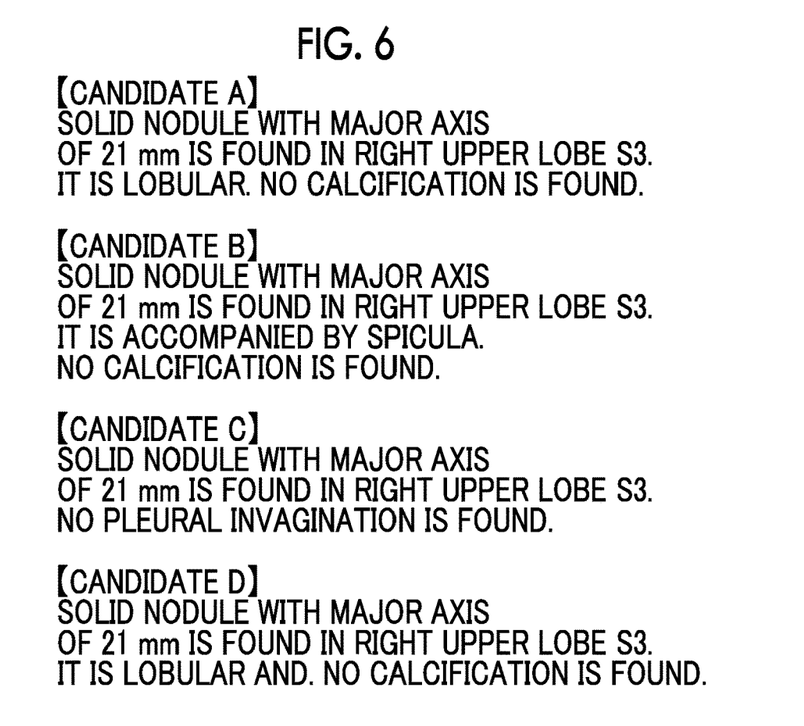
FIG. 6 is a diagram showing an example of comments on findings regarding a medical image.

The generation unit 23 generates, from the medical image G0, a plurality of character strings having different description contents or expressions regarding the medical image G0. FIG. 6 shows candidates for comments on findings as an example of a plurality of character strings regarding the nodular shadow N included in the medical image G0. As a method of generating the comments on findings by using the generation unit 23, for example, a learning model in which machine learning is performed, such as the recurrent neural network described in JP2019-153250A can be applied. In the case of applying such a learning model, the generation unit 23 may generate comments on findings by the generation unit 23 analyzing the medical image G0 via CAD or the like separately from the determination performed by the determination unit 22, and inputting the result of the analysis performed by the generation unit 23 into the learning model. Further, the comments on findings may be generated by inputting the result of the determination performed by the determination unit 22 into the learning model.

Incidentally, the content of the comments on findings generated by the generation unit 23 does not always match the property of the nodular shadow N included in the medical image G0. For example, it is assumed that the above learning model learns a lot of learning data in which "solidity" and "spicula" are included in the same sentence as learning data related to nodular shadows. In this case, if a "solid" nodular shadow N is found in the medical image G0 for which the comments on findings are generated, a sentence including "solidity" and "spicula" may be generated in some cases even though "spicula" is not found in the target nodular shadow N.

Further, it is preferable that the number of characters included in the comments on findings or the number of items corresponding to the property items included in the comments on findings is appropriate for the comments on findings described in the interpretation report. For example, some radiologists prefer concise comments on findings with a small number of characters or items, while others prefer comments on findings that are rich in content with a large number of characters or items. Furthermore, it is preferable that the comments on findings described in the interpretation report are natural as a natural language, that is, fluent.

Therefore, the derivation unit 24 according to the present exemplary embodiment derives a recommended score indicating the degree of recommendation for describing a comment on findings in a document for each of a plurality of comments on findings generated by the generation unit 23 based on the result of the determination performed by the determination unit 22. Specifically, the derivation unit 24 derives a first score, a second score, and a third score for each of the plurality of comments on findings, and derives a recommended score based on the first to third scores. The first score is a score indicating the degree to which the content of the comments on findings matches the result of the determination performed by the determination unit 22. The second score is a score indicating the degree to which the number of characters included in the comments on findings or the number of items corresponding to the property items included in the comments on findings is appropriate. The third score is a score indicating the degree of fluency of the comments on findings.

Figure 7:
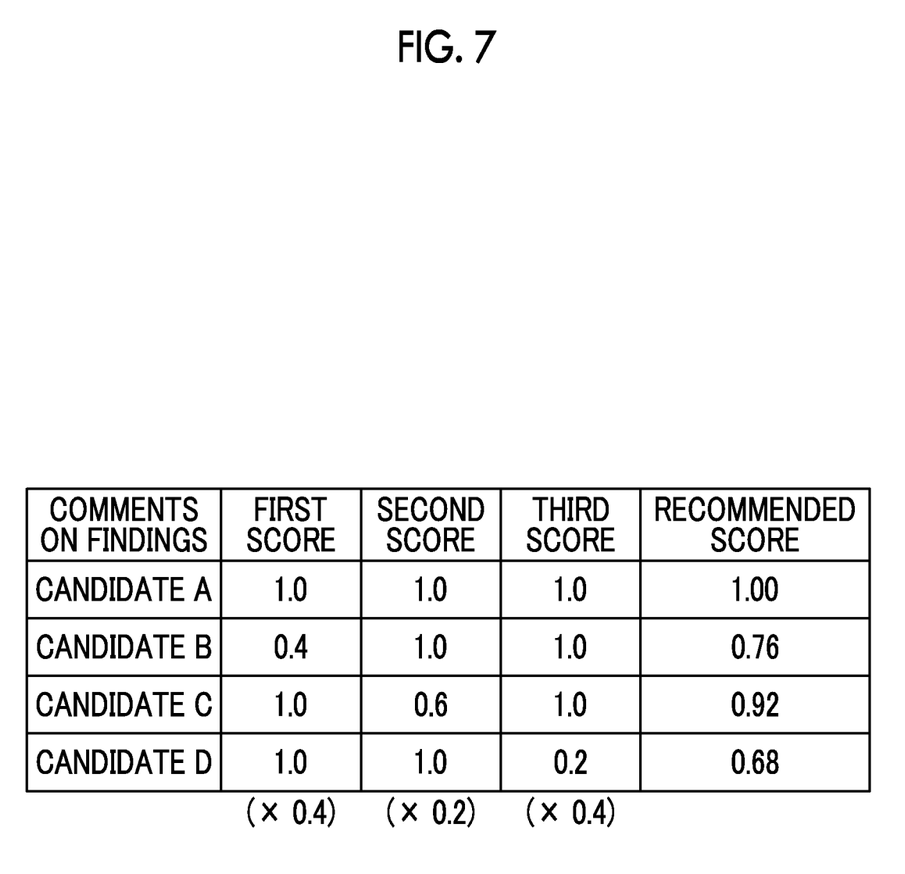
FIG. 7 is a diagram showing an example of a recommended score according to a first exemplary embodiment.

The first to third scores derived by the derivation unit 24 will be described with reference to FIGS. 5 to 7. FIG. 7 shows an example of the first to third scores and the recommended score derived for each of the plurality of comments on findings shown in FIG. 6. Each score shown in FIG. 7 has a maximum value of 1 and a minimum value of 0, and shows that the value is better as the value is closer to 1.

First, the first score will be described. For example, in a case where the result of the determination performed by the determination unit 22 shown in FIG. 5 and the content of each comment on findings shown in FIG. 6 are collated, the contents of the comments on findings of candidates A, C, and D match the results of the determination performed by the determination unit 22. Therefore, the derivation unit 24 derives the first score of the comments on findings of candidates A, C, and D as 1.0. On the other hand, the determination result of "margin/spicula" performed by the determination unit 22 is negative, but the comment on findings of candidate B includes the description "It is accompanied by spicula." Therefore, the content of the comment on findings of candidate B does not partially match the result of the determination performed by the determination unit 22, and the derivation unit 24 derives the first score of candidate B as 0.4, which is lower than that of the other candidates.

Next, the second score will be described. The number of appropriate characters or the number of appropriate items as a reference for deriving the second score may be predetermined or optionally set by the user. For example, it is assumed that the number of appropriate items is six. Candidates A, B and D include six items: position ("right upper lobe S3"), size ("major axis 21 mm"), absorption value ("solid"), lesion type ("nodule"), and shape of the margin ("lobular" or "spicula"), and the presence or absence of calcification. Therefore, the derivation unit 24 determines that the number of items included in the comments on findings of candidates A, B, and D is appropriate, and derives the second score of candidates A, B, and D as 1.0. On the other hand, the comment on findings of Candidate C include only five items: position, size, absorption value, type of lesion, and presence or absence of pleural invagination. Therefore, the derivation unit 24 determines that the number of items corresponding to the property items included in the comment on findings of candidate C is not appropriate, and derives the second score of candidate C as 0.6, which is lower than that of the other candidates.

Next, the third score will be described. Since the comments on findings of candidates A, B, and C are natural as a natural language (English in the example of FIG. 6) and fluent sentences, the derivation unit 24 derives the third score of candidates A, B, and C as 1.0. On the other hand, the comment on findings of Candidate D includes the description "It is lobular and." Therefore, the derivation unit 24 determines that the comment on findings of candidate D includes a part that is not natural as a natural language and is not a fluent sentence, and derives the third score of candidate D as 0.2, which is lower than that of other candidates. As a method for determining whether or not the comment on findings is natural as a natural language, a known typographical error detection method or the like can be applied.

The derivation unit 24 derives the weighted average of the first to third scores derived as described above as a recommended score. FIG. 7 shows a case where the weight of the first score is 0.4, the weight of the second score is 0.2, and the weight of the third score is 0.4 as an example. From the example of FIG. 7, it can be seen that it is most recommended to describe the comments on findings of candidate A having a recommended score of 1.00 in the document. The weight of each score used for deriving the recommended score may be predetermined or may be optionally set by the user. Further, the present disclosure is not limited to the weighted average, and any representative value such as the total of the first to third scores, the arithmetic mean, the maximum value, and the minimum value may be used as a recommended score. Moreover, a recommended score may be derived by selectively using any score from among the first to third scores.

Figure 8:
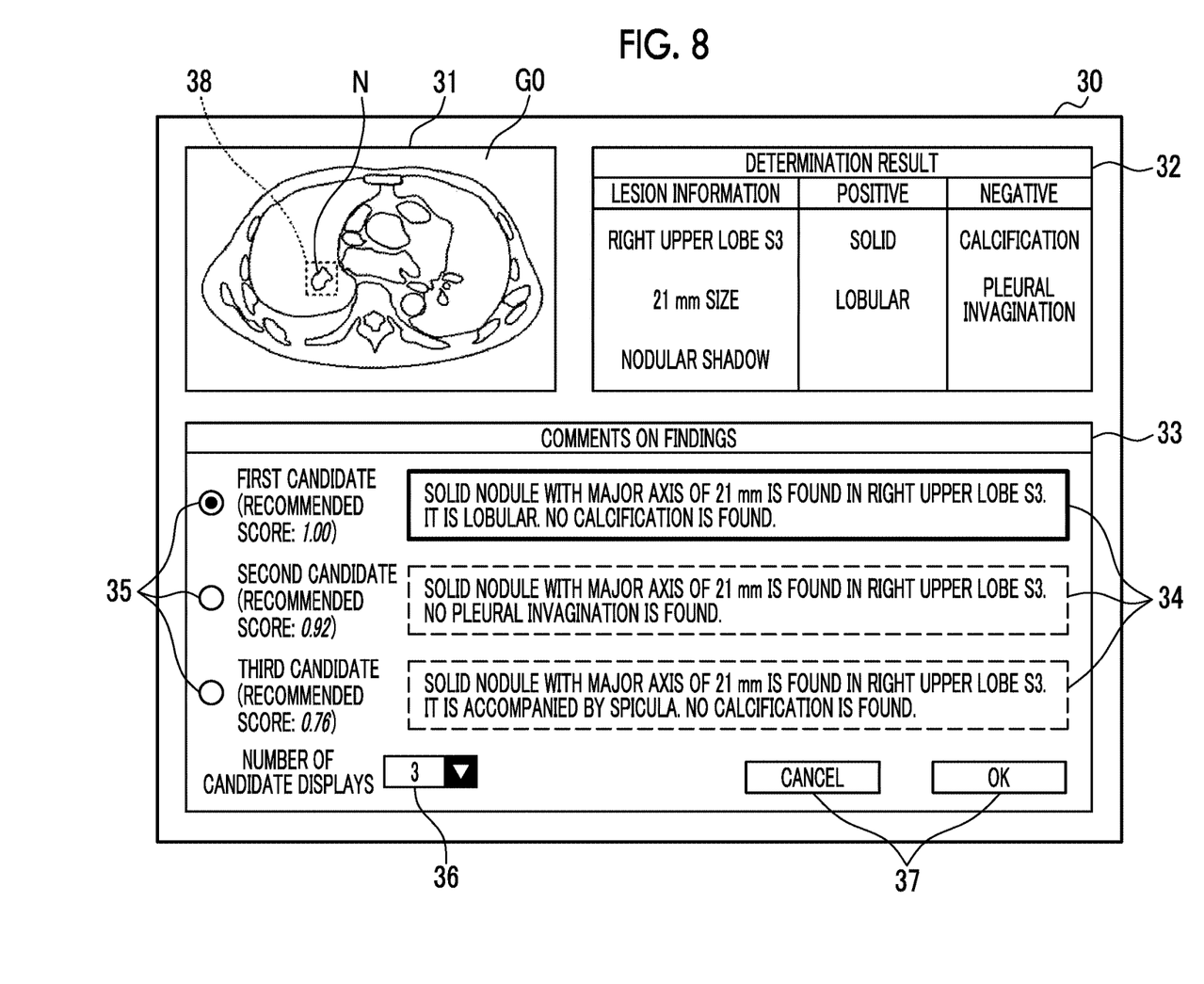
FIG. 8 is a diagram showing an example of a screen for creating an interpretation report according to each exemplary embodiment.

The display control unit 25 performs control such that at least one comment on findings and the recommended score corresponding to the comment on findings are displayed on the display 14. FIG. 8 is a diagram showing an example of the interpretation report creation screen 30 displayed on the display 14. The creation screen 30 includes an image display region 31 on which the medical image G0 is displayed, a determination result display region 32 on which the result of the determination performed by the determination unit 22 is displayed, and a comments-on-findings display region 33 in which candidates for a plurality of comments on findings generated by the generation unit 23 are displayed.

In the comments-on-findings display region 33, at least one text box 34 in which the comments on findings are displayed, a radio button 35 for the user to select any one comment on findings, and a cancel and OK button 37 are displayed. In addition, the recommended score corresponding to the comments on findings displayed in each of the text boxes 34 is also displayed. A pull-down menu 36 for changing the number of candidates for comments on findings displayed in the comments-on-findings display region 33 may be provided so that the user can optionally change the number of candidates for comments on findings displayed on the creation screen 30.

The user selects one of the comments on findings with the radio button 35 while referring to the result of the determination displayed in the determination result display region 32 and the recommended score displayed in the comments-on-findings display region 33. Since the recommended scores corresponding to each comment on findings are displayed on the creation screen 30 according to the present exemplary embodiment, the user can refer to the recommended scores in the case of selecting the comments on findings to be described in the document.

It is preferable that the display control unit 25 performs control such that a plurality of comments on findings are displayed on the display by arranging the comments on findings in the order of recommended scores. In the example of FIG. 8, candidate A, candidate C, and candidate B are displayed as the first candidate, the second candidate, and the third candidate, respectively, in descending order of the recommended score. By arranging the comments on findings in the order of recommended scores in this way, it is possible to support the user in quickly selecting a comment on findings to be described in the document while presenting a plurality of comments on findings.

Further, it is preferable that the display control unit 25 performs control such that the comment on findings having a highest recommended score among the plurality of comments on findings is emphasized and displayed on the display. In the example of FIG. 8, the text box 34 of the comments on findings of the first candidate having the highest recommended score is emphasized in a thick frame. By emphasizing and displaying the comments on findings having the highest recommended score in this way, it is possible to support the user in quickly selecting a comment on findings to be described in the document while presenting a plurality of comments on findings.

Further, the display control unit 25 may perform control such that the comment on findings having the recommended score equal to or higher than a predetermined threshold value among the plurality of comments on findings is displayed on the display. The threshold value may be predetermined, for example, or may be optionally set by the user. As an example, in a case where the threshold value is 0.9, only the comments on findings of candidates A and C are displayed on the display. By displaying the comments on findings having the recommended score equal to or higher than the predetermined threshold value in this way, only the comments on findings having a high degree of recommendation can be presented. Therefore, it is possible to support the user in quickly selecting a comment on findings to be described in the document.

Figure 9:
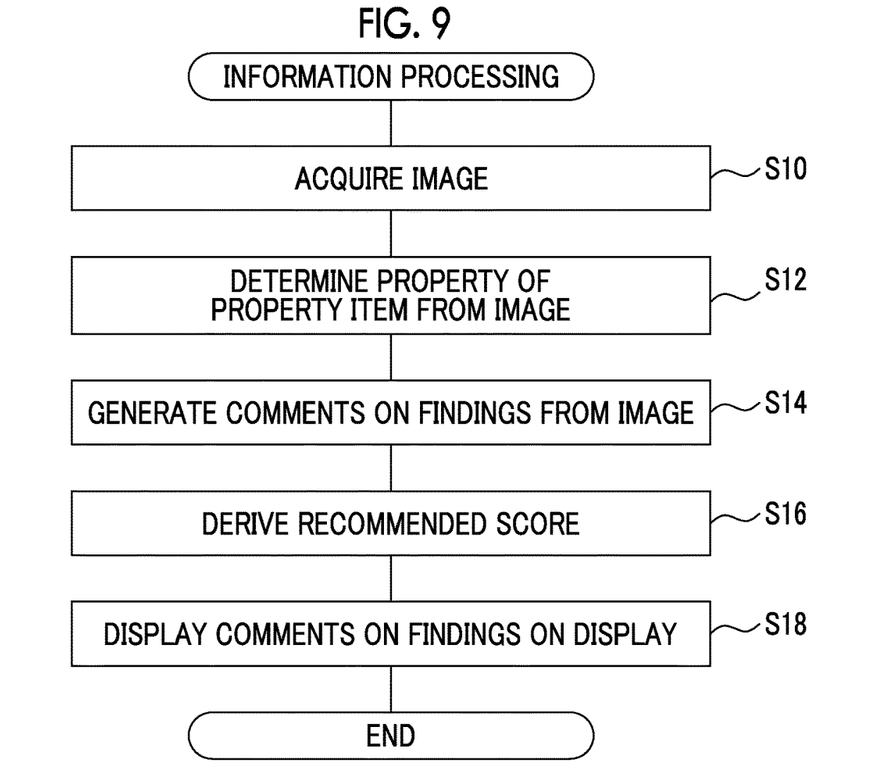
FIG. 9 is a flowchart showing an example of information processing according to each exemplary embodiment.

Next, with reference to FIG. 9, operations of the information processing apparatus 20 according to the present exemplary embodiment will be described. The CPU 11 executes the information processing program 12, and thus, the information processing shown in FIG. 9 is executed. The information processing shown in FIG. 9 is executed, for example, in a case where an instruction to start creating an interpretation report for the medical image G0 is input via the input unit 15.

In Step S10 of FIG. 9, the acquisition unit 21 acquires the medical image G0 from the image server 5. In Step S12, the determination unit 22 specifies the position, type, and size of the lesion included in the medical image G0 acquired in Step S10, and determines the properties of predetermined property items related to the specified lesion. In Step S14, the generation unit 23 generates comments on findings regarding the medical image G0 from the medical image G0. The processes of Step S12 and Step S14 may be performed in parallel or in reverse order.

In Step S16, the derivation unit 24 derives a recommended score for each comment on findings generated in Step S14 based on the result of the determination in Step S12. In Step S18, the display control unit 25 performs control such that the comments on findings generated in Step S14 and the recommended score corresponding to the comments on findings are displayed on the display 14, and ends the process.

As described above, the information processing apparatus 20 according to the present exemplary embodiment derives a recommended score based on the first score, the second score, and the third score. Therefore, a comment on findings whose content matches the result of the determination, having an appropriate number of characters or an appropriate number of items corresponding to the property items, and having a high degree of fluent sentences can be presented as a recommended comment on findings. Thus, it is possible to support the user in creating a document such as an interpretation report.

Second Exemplary Embodiment

Next, a second exemplary embodiment of the present disclosure will be described. In the information processing apparatus 20 according to the present exemplary embodiment, the determination unit 22 outputs a fourth score together with the determination of the property, and the derivation unit 24 derives a recommended score based on the fourth score instead of the first to third scores. The configuration of the medical information system 1 (see FIG. 1) and the hardware configuration of the information processing apparatus 20 (see FIG. 2) according to the present exemplary embodiment are the same as those in the first exemplary embodiment, and thus the description thereof will be omitted. Further, a duplicate description of the functional configuration of the information processing apparatus 20 (see FIG. 3) will be omitted.

The determination unit 22 derives a fourth score indicating the prominence of the properties of the predetermined property items from at least one medical image G0. Then, the property is determined based on the fourth score. The "prominence of properties" means a degree to which the characteristics of the properties appear in the medical image G0 to be determined, in other words, it can be said to be a confidence degree of the result of the determination performed by the determination unit 22. Specifically, the determination unit 22 analyzes the medical image G0 via CAD or the like, and specifies the position, type, and size of the lesion included in the medical image G0. Then, it is determined whether or not the characteristic of the property of the predetermined property item related to the specified lesion appears in the medical image G0, and the fourth score is derived according to the prominence of the characteristic. The determination unit 22 may determine, for example, a property item whose fourth score is equal to or higher than the threshold value as positive.

Figure 10:
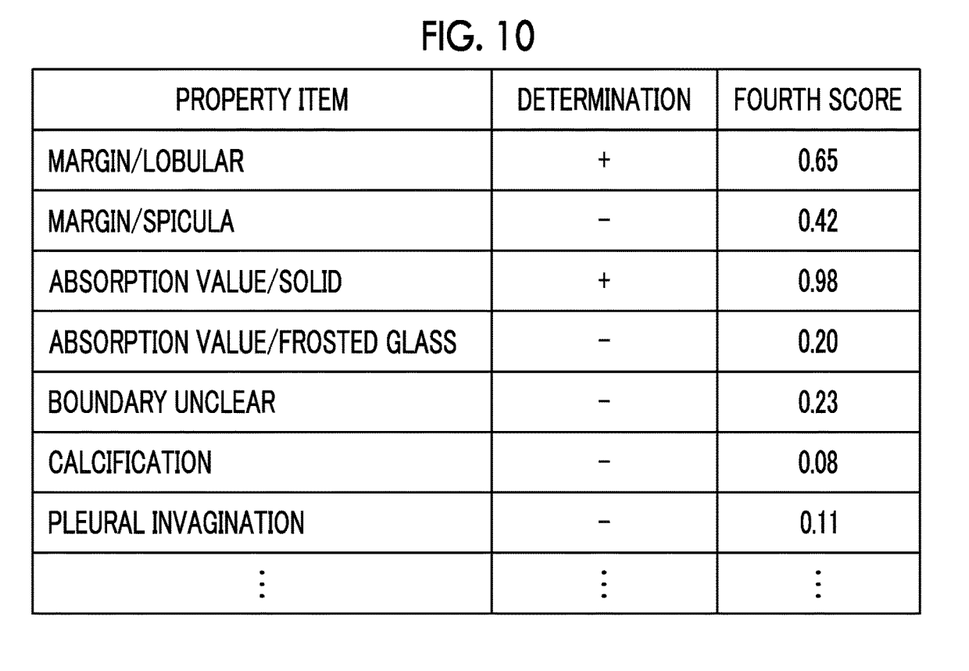
FIG. 10 is a diagram showing an example of a fourth score according to a second exemplary embodiment.

FIG. 10 shows an example of the result of determining the properties of the property items related to the nodular shadow N in FIG. 4 and the fourth score. The fourth score has a maximum value of 1 and a minimum value of 0, and shows that the prominence of the property of the corresponding property item is higher as the value is closer to 1. For example, in the example of FIG. 10, since the fourth score of "absorption value/solid" is close to 0.98 and 1, it can be seen that the solidity is prominently found in the nodular shadow N. On the other hand, since the fourth score of "calcification" is 0.08, which is close to 0, it can be seen that almost no calcification is found in the nodular shadow N.

Figure 11:
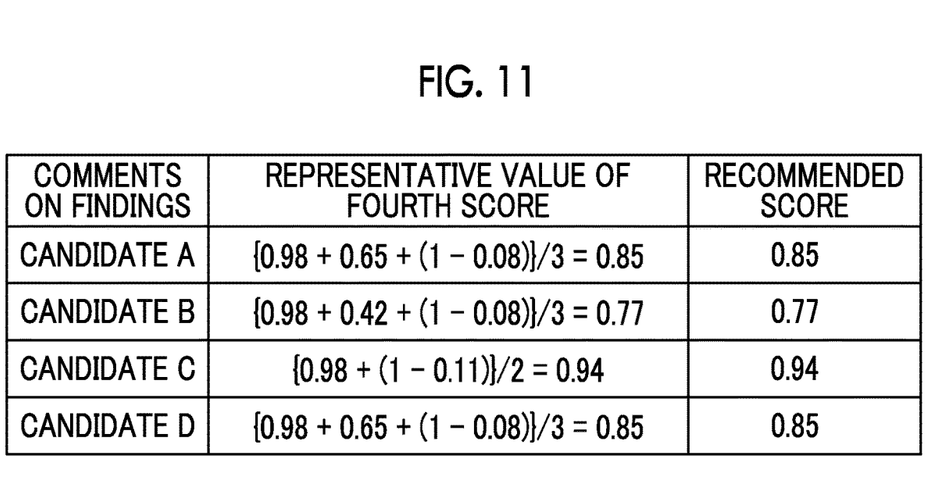
FIG. 11 is a diagram showing an example of a recommended score according to the second exemplary embodiment.

The derivation unit 24 derives a recommended score based on the fourth score corresponding to the item corresponding to the property item included in the comments on findings generated by the generation unit 23. FIG. 11 shows recommended scores for each of the comments on findings of candidates A to D in FIG. 6, which were derived based on the fourth score of FIG. 10. For example, in the comments on findings of candidate A, the description of the item corresponding to the property item of "absorption value/solid" ("solidity"), the description of the item corresponding to the property item of "margin/lobular" ("lobulation"), and the description of the item corresponding to the property item of "calcification" ("no calcification is found") are included. The derivation unit 24 derives the recommended score based on the fourth scores 0.98, 0.65, and 0.08 corresponding to each of these items. In the example of FIG. 11, the arithmetic mean of the fourth score is used as the recommended score, but the present disclosure is not limited thereto, and for example, any representative value such as the sum of the fourth scores, the weighted average, the maximum value, and the minimum value can be used.

In addition, in a case where a property item having a low fourth score is described as a negative sentence, such as the description "no calcification is found" in the comments on findings of candidate A, the content of the comments on findings matches the result of the determination performed by the determination unit 22. Therefore, as illustrated in FIG. 11, the value of (1-0.08) may be used as the fourth score corresponding to the property item of "calcification."

As described above, the information processing apparatus 20 according to the present exemplary embodiment derives a recommended score based on the fourth score. Therefore, it is possible to present a comment on findings strongly showing the characteristics of the properties in the medical image G0 to be determined and describing property items with a high confidence degree of the result of the determination performed by the determination unit 22 as a recommended comment on findings, and to support the user in creating a document such as an interpretation report.

Third Exemplary Embodiment

Next, a third exemplary embodiment of the present disclosure will be described. In the information processing apparatus 20 according to the present exemplary embodiment, the derivation unit 24 derives a recommended score based on a fifth score instead of the first to fourth scores. The configuration of the medical information system 1 (see FIG. 1) and the hardware configuration of the information processing apparatus 20 (see FIG. 2) according to the present exemplary embodiment are the same as those in the first exemplary embodiment, and thus the description thereof will be omitted. Further, a duplicate description of the functional configuration of the information processing apparatus 20 (see FIG. 3) will be omitted.

Figure 12:
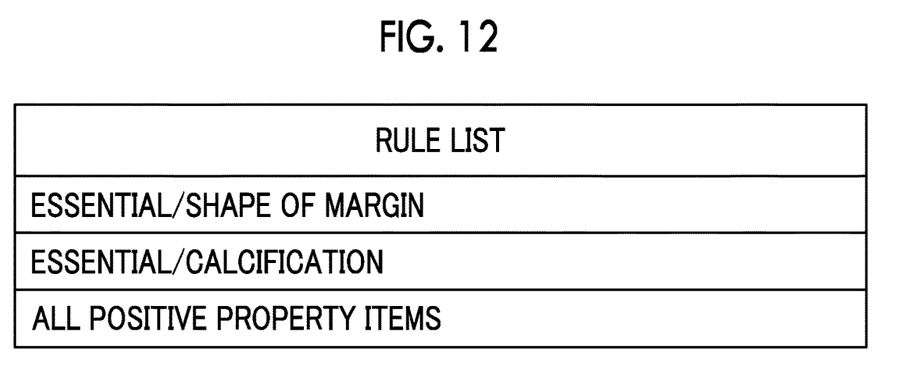
FIG. 12 is a diagram showing an example of a rule according to a third exemplary embodiment.

The derivation unit 24 derives a fifth score indicating the degree to which the content of the comments on findings conforms to a predetermined rule for each of the plurality of comments on findings, and derives a recommended score based on the fifth score. The predetermined rule is a rule predetermined for each type of lesion regarding how to select the property item to be described in the comments on findings, and is stored in the storage unit 13. FIG. 12 shows an example of a rule regarding the property item regarding the nodular shadow N in FIG. 4. As the rules, for example, rules for property items that should be described ("essential/shape of margin" and the like), rules according to the property ("all positive property items" and the like), and the like can be used.

Figure 13:
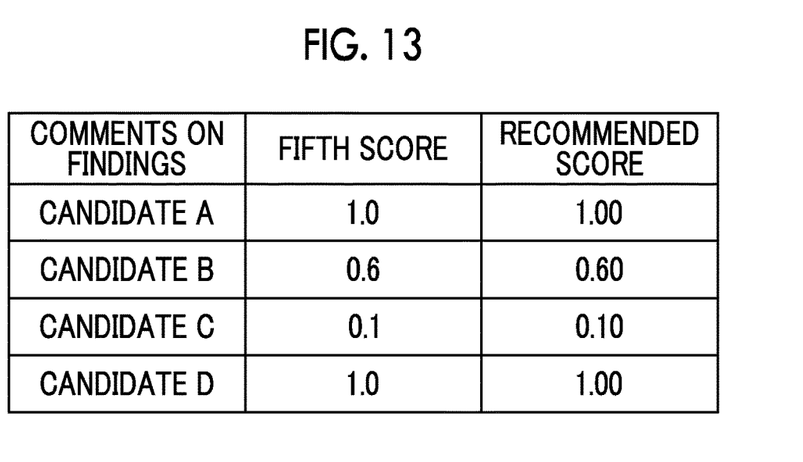
FIG. 13 is a diagram showing an example of a fifth score and a recommended score according to the third exemplary embodiment.

FIG. 13 shows an example of the fifth score and recommended score derived for each of the plurality of comments on findings shown in FIG. 6. The fifth score has a maximum value of 1 and a minimum value of 0, and shows that the content of the comments on findings conforms to the rule as the value is closer to 1. For example, in a case where the rule shown in FIG. 12 is collated with the content of each comment on findings shown in FIG. 6, the content of the comments on findings of candidates A and D conforms to all the rules shown in FIG. 12. Therefore, the derivation unit 24 derives the fifth score of the comments on findings of candidates A and D as 1.0.

On the other hand, although the determination result of "margin/lobular" performed by the determination unit 22 is positive (see FIG. 5), in the comment on findings of candidate B, there is no description about the lobulation. Therefore, the content of the comment on findings of candidate B does not conform to the rule of "all positive property items", and the derivation unit 24 derives the fifth score of candidate B as 0.6, which is lower than the comments on findings of candidates A and D. In addition, in the comment on findings of candidate C, there is no description about the shape of the margin and calcification, and there is no description about the lobulation that is determined to be positive. Therefore, the content of the comment on findings of candidate C does not conform to the rules of "essential/shape of margin", "essential/calcification", and "all positive property items", and the derivation unit 24 derives the fifth score of candidate C as 0.1, which is lower than the comments on findings of candidates A, B, and D. The derivation unit 24 derives the fifth score derived as described above as a recommended score.

As described above, the information processing apparatus 20 according to the present exemplary embodiment derives a recommended score based on the fifth score. Therefore, it is possible to present a comment on findings with a high degree to which the content of the comments on findings conforms to a predetermined rule as a recommended comment on findings, and to support the user in creating a document such as an interpretation report.

As the predetermined rule, the rule predetermined by the user may be used. For example, prior to the derivation of the fifth score performed by the derivation unit 24, the display control unit 25 may display a screen provided with a check box for selecting any rule from a plurality of predetermined rules on the display 14 and receive the selection by the user.

Figure 14:
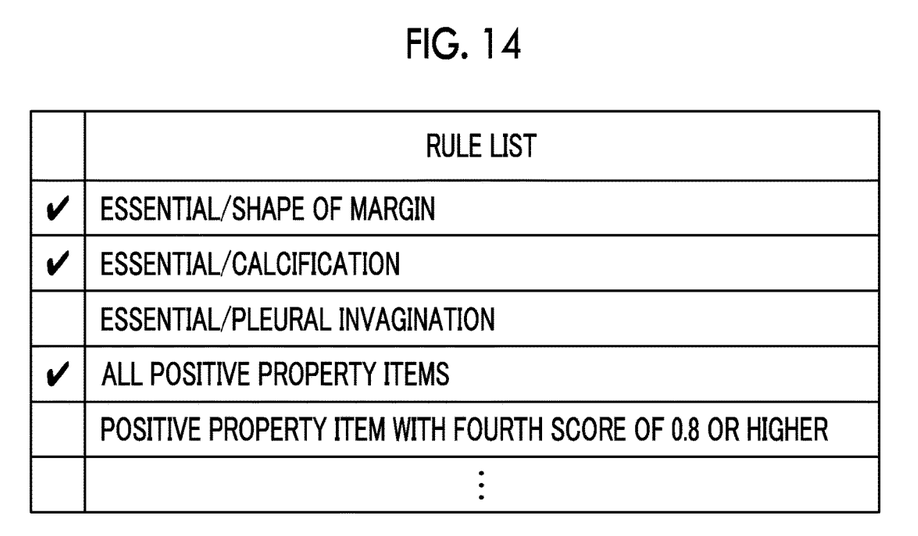
FIG. 14 is a diagram showing an example of a rule determined by a user according to the third exemplary embodiment.

FIG. 14 is a diagram showing an example in which the rules of "essential/shape of margin", "essential/calcification", and "all positive property items" are selected by the user from among a plurality of predetermined rules. In this case, the derivation unit 24 derives the fifth score according to the degree to which the content of each comment on findings conforms to the selected rule. In this way, by using the rules predetermined by the user, it is possible to present the comments on findings according to a user's preference as a recommended comment on findings, and to support the user in creating a document such as an interpretation report.

Further, the derivation unit 24 may derive a sixth score indicating the degree to which the content of the character string for analysis conforms to the rule for each of the plurality of predetermined rules, and may derive the fifth score for each of the plurality of comments on findings using the sixth score of the rule to which the content of the comment on findings conforms. The character string for analysis is, for example, a comment on findings described in an interpretation report created in the past (hereinafter referred to as a "past comment on findings").

Figure 15:
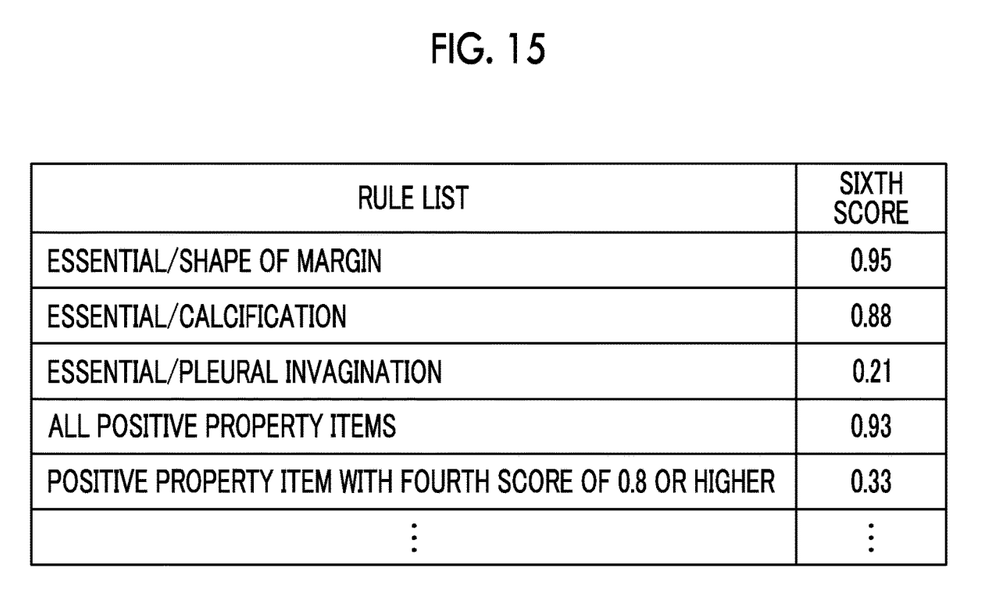
FIG. 15 is a diagram showing an example of a sixth score according to the third exemplary embodiment.

FIG. 15 shows the sixth score derived from the content of past comments on findings for each of the plurality of predetermined rules. For example, it is assumed that 95% of the past comments on findings include a description about the shape of the margin. In this case, the derivation unit 24 derives the sixth score regarding "essential/shape of margin" as 0.95.

Further, in a case where the medical image is included in the interpretation report created in the past, the derivation unit 24 may analyze the medical image to determine the property, and derive a sixth score regarding the rule according to the property from the content of the comments on findings corresponding to the medical image. For example, it is assumed that 93% of the past comments on findings include descriptions about all positive property items included in the medical image corresponding to the comments on findings. In this case, the derivation unit 24 derives the sixth score regarding "all positive property items" as 0.93.

Figure 16:
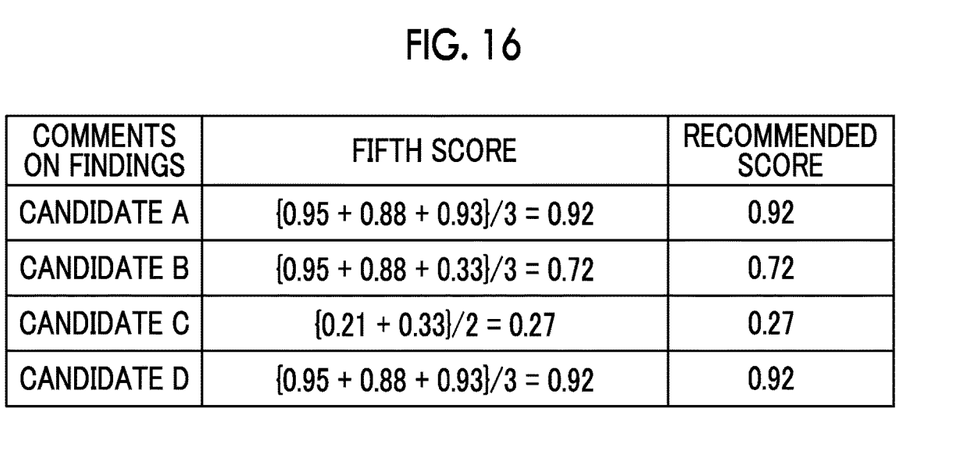
FIG. 16 is a diagram showing an example of a fifth score and a recommended score according to the third exemplary embodiment.

FIG. 16 shows the fifth score and the recommended score for each of the comments on findings of candidates A to D in FIG. 6, which were derived based on the sixth score of FIG. 15. For example, the comments on findings of candidate A conform to the respective rules of "essential/shape of margin", "essential/calcification", and "all positive property items." The derivation unit 24 derives the fifth score based on the sixth scores 0.95, 0.88, and 0.93 corresponding to each of these rules. In the example of FIG. 16, the arithmetic mean of the sixth score of the rule to which the comments on findings conform is used as the fifth score, but the present disclosure is not limited thereto, and for example, any representative value such as the sum of the sixth scores, the weighted average, the maximum value, and the minimum value can be used.

Further, as a predetermined rule, a rule having a sixth score equal to or higher than the threshold value may be used. For example, in a case where the threshold value is 0.5, the rules of "essential/shape of margin", "essential/calcification", and "all positive property items" in FIG. 15 are predetermined rules. Therefore, the derivation unit 24 derives the degree of conforming to these rules as the fifth score.

In this way, by deriving the fifth score using the sixth score derived from the contents of the character string for analysis and using the fifth score as the recommended score, the comments on findings similar to the trends described in the past can be presented as recommended comments on findings. Therefore, it is possible to support the user in creating a document such as an interpretation report.

As described above for each exemplary embodiment, with the information processing apparatus 20 according to each exemplary embodiment of the present disclosure, a property of a predetermined property item from at least one medical image G0 is determined, a plurality of comments on findings related to the medical image G0 are generated from the medical image G0, and a recommended score indicating the degree of recommendation for describing the comment on findings in a document for each of the plurality of comments on findings is derived based on the result of the determination. By deriving such a recommended score, it is possible to quantitatively compare the comments on findings that are recommended to be described in the document, and to thereby improve the quality of the comments on findings presented to the user. Therefore, it is possible to support the user in creating a document such as an interpretation report.

The first to fifth scores derived in each of the above exemplary embodiments may be combined as appropriate.

Figure 17:
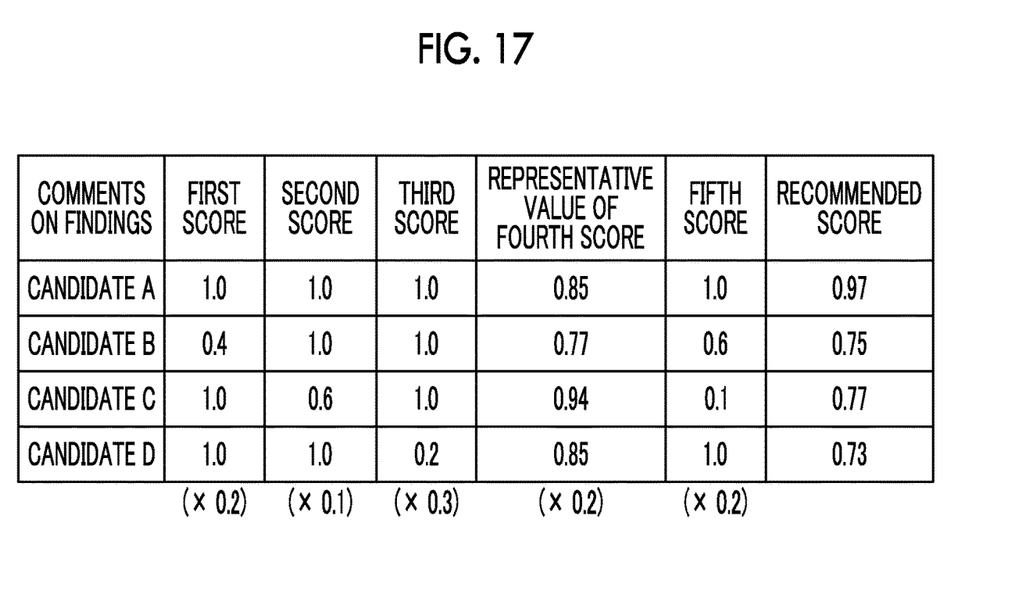
FIG. 17 is a diagram showing an example of a recommended score according to each exemplary embodiment.

For example, FIG. 17 shows the first to fifth scores for each of the comments on findings of candidates A to D in FIG. 6 and the recommended scores derived based on the weighted average of the first to fifth scores. FIG. 17 shows a case where the weight of the first score, the representative value of the fourth score, and the fifth score is 0.2, the weight of the second score is 0.1, and the weight of the third score is 0.3 as an example. The weight of each score used for deriving the recommended score may be predetermined or may be optionally set by the user. Further, instead of the weighted average, any representative value such as the total of the first to fifth scores, the arithmetic mean, the maximum value, and the minimum value may be used as a recommended score.

Further, in each of the above exemplary embodiments, the determination unit 22 specifies the position of the lesion included in the medical image G0, but the present disclosure is not limited thereto. For example, the user may select a region of interest in the medical image G0 via the input unit 15, and the determination unit 22 may determine the properties of the property items of the lesion included in the selected region. According to such a form, for example, even in a case where one medical image G0 includes a plurality of lesions, it is possible to support creation of comments on findings for the lesion desired by the user.

Further, in each of the above exemplary embodiments, the display control unit 25 may generate an image in which a mark indicating the position of lesion specified by the determination unit 22 is added to the medical image G0. For example, in the example of FIG. 8, the nodular shadow N included in the medical image G0 is surrounded by a broken-line rectangle 38. This makes it easier, for example, for a reader of the interpretation report to see the region in the image that is the basis of the lesion, without the need for the radiologist to provide comments on findings related to the position of the lesion. Therefore, it is possible to support creation of a document such as the interpretation report. The mark indicating the positions of the lesion is not limited to the broken-line rectangle 38, but may be various marks such as, for example, a polygon, a circle, an arrow, or the like, and the line type of the mark (a solid line, a broken line, and a dotted line), line color, line thickness, or the like may be changed as appropriate.

Further, in each of the above exemplary embodiments, each process of the determination unit 22, the generation unit 23, and the derivation unit 24 in the information processing apparatus 20 encompassed in the interpretation WS 3 may be performed by an external apparatus, for example, another analysis server connected to the network 10. In this case, the external apparatus acquires the medical image G0 from the image server 5, determines the properties of the predetermined property items from the medical image G0, generates a plurality of comments on findings related to the medical image G0, and derives a recommended score indicating the degree of recommendation for describing the comment on findings in the document for each of the plurality of comments on findings based on the result of determining the properties. In the information processing apparatus 20, the display control unit 25 controls the display content to be displayed on the display 14 based on the properties determined by the external apparatus, the plurality of comments on findings generated by the external apparatus, and the recommended score derived from the external apparatus.

Further, in each of the above exemplary embodiments, the present disclosure is applied in the case where an interpretation report is created as a document and comments on findings are generated as a character string, but the present disclosure may be applied at the time of creating medical documents other than the interpretation report, such as an electronic medical record and a diagnostic report, and documents containing character string related to other images.

Further, in each of the above exemplary embodiments, although the various processes are performed using the medical image G0 with the lung as the diagnosis target, the diagnosis target is not limited to the lung. In addition to the lung, any part of a human body such as a heart, liver, brain, and limbs can be diagnosed. Further, in each of the above exemplary embodiments, various processes are performed using one medical image G0, but various processes may be performed using a plurality of images such as a plurality of tomographic images relating to the same diagnosis target.

In each of the above exemplary embodiments, for example, as hardware structures of processing units that execute various kinds of processing, such as the acquisition unit 21, the determination unit 22, the generation unit 23, the derivation unit 24, and the display control unit 25, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor. As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

The disclosure of JP2020-025672 filed on Feb. 18, 2020 is incorporated herein by reference in its entirety. All literatures, patent applications, and technical standards described herein are incorporated by reference to the same extent as if the individual literature, patent applications, and technical standards were specifically and individually stated to be incorporated by reference.

What is claimed is:

1. An information processing apparatus comprising at least one processor, wherein the at least one processor is configured to:
  determine a property of a predetermined property item from at least one image;
  generate a plurality of character strings related to the at least one image from the at least one image;

derive a recommended score indicating a degree of recommendation for describing the character string in a document for each of the plurality of character strings based on a result of the determination;

perform a control to display the plurality of character strings on a display by arranging the plurality of character strings in an order of the recommended scores; and for each of the plurality of character strings, derive
- a first score indicating a degree to which a content of the character string matches the result of the determination,
- a second score indicating a degree to which the number of characters included in the character string or the number of items corresponding to the property items included in the character string is appropriate, and
- a third score indicating a degree of fluency of the character string; and derive the recommended score based on the first to third scores.

2. The information processing apparatus according to claim 1, wherein the at least one processor is configured to:
   derive a fourth score indicating a prominence of the property from the image; and
   derive the recommended score based on the fourth score corresponding to the item corresponding to the property item included in the character string.

3. The information processing apparatus according to claim 1, wherein the at least one processor is configured to:
   for each of the plurality of character strings, derive a fifth score indicating a degree to which a content of the character string conforms to a predetermined rule; and
   derive the recommended score based on the fifth score.

4. The information processing apparatus according to claim 3, wherein the rule is a rule predetermined by a user.

5. The information processing apparatus according to claim 3, wherein the at least one processor is configured to:
   for each of a plurality of predetermined rules, derive a sixth score indicating a degree to which a content of a character string for analysis conforms to the rule; and
   for each of the plurality of character strings, derive the fifth score by using the sixth score of the rule to which the content of the character string conforms.

6. The information processing apparatus according to claim 1, wherein the at least one processor is configured to perform control such that at least one character string and the recommended score corresponding to the character string are displayed on a display.

7. The information processing apparatus according to claim 1 wherein the at least one processor is configured to perform control such that the character string having the recommended score equal to or higher than a predetermined threshold value among the plurality of character strings is displayed on the display.

8. The information processing apparatus according to claim 1, wherein the at least one processor is configured to perform control such that the character string having a highest recommended score among the plurality of character strings is emphasized and displayed on the display.

9. An information processing method comprising:
   determining a property of a predetermined property item from at least one image;
   generating a plurality of character strings related to the image from the image;
   deriving a recommended score indicating a degree of recommendation for describing the character string in a document for each of the plurality of character strings based on a result of the determination;
   performing a control to display the plurality of character strings on a display by arranging the plurality of character strings in an order of the recommended scores; and
   for each of the plurality of character strings, deriving
   - a first score indicating a degree to which a content of the character string matches the result of the determination,
   - a second score indicating a degree to which the number of characters included in the character string or the number of items corresponding to the property items included in the character string is appropriate, and
   - a third score indicating a degree of fluency of the character string; and
   derive the recommended score based on the first to third scores.

10. A non-transitory computer-readable storage medium storing an information processing program for causing a computer to execute a process comprising:
    determining a property of a predetermined property item from at least one image;
    generating a plurality of character strings related to the image from the image; deriving a recommended score indicating a degree of recommendation for describing the character string in a document for each of the plurality of character strings based on a result of the determination;
    performing a control to display the plurality of character strings on a display by arranging the plurality of character strings in an order of the recommended scores; and
    for each of the plurality of character strings, deriving
    - a first score indicating a degree to which a content of the character string matches the result of the determination,
    - a second score indicating a degree to which the number of characters included in the character string or the number of items corresponding to the property items included in the character string is appropriate, and
    - a third score indicating a degree of fluency of the character string; and
    derive the recommended score based on the first to third scores.

* * * * *